United States Patent [19]

Harris et al.

[11] Patent Number: 5,332,673
[45] Date of Patent: Jul. 26, 1994

[54] APPLICATION OF NATIVE SOIL BACTERIA AS SELECTIVE BIOLOGICAL CONTROL AGENTS OF THE WEEDS DOWNY BROME, JAPANESE BROME, AND JOINTED GOATGRASS IN WHEAT

[75] Inventors: Pamela A. Harris; Phillip W. Stahlman, both of Hays, Kans.

[73] Assignee: Kansas State University Research Foundation, Manhattan, Kans.

[21] Appl. No.: 28,556

[22] Filed: Mar. 8, 1993

[51] Int. Cl.$^5$ .................... C12N 1/20; A01N 63/02
[52] U.S. Cl. ................... 435/253.3; 504/117; 435/252.1; 435/252.4
[58] Field of Search ............... 435/253.3, 252.1, 252.4; 504/117; A01N 63/02

[56] References Cited

U.S. PATENT DOCUMENTS

| | | | |
|---|---|---|---|
| 4,758,518 | 7/1988 | Taylor | 435/253.3 |
| 4,948,413 | 8/1990 | Maekawa et al. | 504/130 |
| 5,030,562 | 7/1991 | Elliott et al. | 435/29 |

FOREIGN PATENT DOCUMENTS

WO9013224 11/1990 PCT Int'l Appl. .

OTHER PUBLICATIONS

Kennedy et al.; Rhizobacteria Suppressive to Theweed Downy Brome; Soil Sci. Soc. Am. J., vol. 55, May-Jun. 1991.
Agronomy Abstracts, 1990 Annual Meetings, Oct. 21-26, 1990, San Antonio, Tex. Harris et al., Selective Control of Winter Annual Grass Weeds in Winter Wheat With Soil Bacteria, Abstract.
Kennedy et al.; Root-Colonizing Bacteria as Biological Control Agents for Downy Brome in Winter Wheat Cropping System; Apr. 23, 1991.
Kennedy et al "Rhizohacteria Suppressive to the Weed Downy Brome" *Soil Sci Soc Am. J.* 55: 722-727 1991.
Johnson et al. "Suppression of Downy Brome Growth by a Rhizobacterium in Controlled Environments", *Soil Sci Soc Am J.* 57: 73-77, 1993.
Annual Research Progress Report "Pseudomonads as a Biological Control Agent for Downy Brome in Winter Wheat" 1993.

*Primary Examiner*—Richard L. Raymond
*Assistant Examiner*—S. Mark Clardy
*Attorney, Agent, or Firm*—Hovey, Williams, Timmons & Collins

[57] ABSTRACT

Novel modified and unmodified soil and rhizo-plane bacterial strains are disclosed which are useful for the control of weeds (e.g., downy brome, Japanese brome, and jointed goatgrass) in the vicinity of wheat. The specific bacteria are identified as *Pseudomonas putida* (FH160), Enterobacter taylorae (FH650), and *Xanthomonas maltophilia* (FH131). A method of weed control using one or more of the bacterial strains is provided, which can be effected by spraying or direct soil application during planting of bacterial solutions. The strains can also be mixed with chemical herbicides to give enhanced weed control.

4 Claims, No Drawings

APPLICATION OF NATIVE SOIL BACTERIA AS SELECTIVE BIOLOGICAL CONTROL AGENTS OF THE WEEDS DOWNY BROME, JAPANESE BROME, AND JOINTED GOATGRASS IN WHEAT

BACKGROUND OF THE INVENTION

1. Field of the Invention

The present invention is broadly concerned with novel, isolated strains of bacteria (as well as modifications thereof) having the ability to control the weeds downy brome, Japanese brome, and/or jointed goatgrass. More particularly, it is concerned with a bacterial strain selected from the group consisting of *Pseudomonas putida* (FH160), *Enterobacter taylorae* (FH650), and *Xanthomonas maltophilia* (FH131) and mixtures thereof, and a method of use thereof in an area of planted wheat for weed control.

2. Description of the Prior Art

The widespread adoption of conservation tillage systems in semi-arid environments and a shift from standard-height to semidwarf wheat (*Triticum aestivum L.*) cultivars have been accompanied by a dramatic increase and spread of winter annual grass weeds in winter wheat (Morrow and Stahlman, *Weed Science* 32 (Suppl. 1):2-6 (1984); Wicks, In: Weed Control in Limited-Tillage Systems, A. F. Wiese (ed.), pages 77-92, Monograph 2, Weed Science Society of America (1985)). Downy brome (*Bromus tectorum L.*) and the related species Japanese brome (*B. japonicus Thunb.*) and cheat (*B. secalinus L.*) infest more than 14 million acres of wheat in the western United States (Kennedy et al., *Soil Science Society of America Journal* 55:722-727 (1991)), and up to 1 million acres are infested annually with bromes in Kansas (Harris and Stahlman, *Agronomy Abstracts*, page 250, American Society of Agronomy (1991)). Jointed goatgrass (*Aegilops cylindrica Host.*) is another increasingly troublesome grass weed because it out-crosses with wheat. Jointed goatgrass infests an estimated 3-4 million acres of wheat in 10 Great Plains and western states, including about 400,000 acres in Kansas (Donald and Ogg, *Weed Technology* 5:3-17 (1991)).

Studies indicate that downy brome can be highly competitive with winter wheat (Stahlman and Miller, *Weed Science* 38:224-228 (1990)). Densities of 24, 40, and 65 down brome plants $m^{-2}$ reduced winter wheat yields by 10, 15, and 20%, respectively, when the downy brome emerged within 14 days after wheat emergence. Annual brome densities of 100 to 200 plants $m^{-2}$ are common and occasionally exceed 400 $m^{-2}$.

Metribuzin [4-amino-6-(1,1-dimethylethyl)-3-(methylthio)-1,2,4-triazin-5(4H)-one] is the only herbicide registered for postemergence control of *Bromus spp.* in a few tolerant winter wheat cultivars, but its high cost and restriction to tolerant cultivars have limited acceptance and use. More recently, diclofop [($\pm$)-2-(4-(2,4-dichlorophenoxy) phenoxy)propanoic acid], triallate [S-(2,3,3-trichloro-2-propenyl)bis(1-methylethyl)carbamothioate], and trifluralin [2,6-dinitro-N,N-dipropyl-4-(trifluoromethyl)benzenamine] were registered for preplant application to control certain Bromus spp. However, growers prefer postemergence herbicides because the density of annual bromes can vary widely and they want to assess the need before applying herbicides. Trifluralin is the only herbicide registered for suppression or partial control of jointed goatgrass.

Bacteria can suppress plant growth by the production of phytotoxic substances absorbed by the plant root (Suslow and Schroth, *Phytopathology* 72:111-115 (1982)). The inhibitory influence of these antagonistic bacteria has been shown to be both species and cultivar specific (Elliott and Lynch, *Soil Biology and Biochemistry* 16:69-71 (1984)). Because of this specificity, these bacteria have potential for controlling weeds growing in crops.

Microbial herbicides are indigenous living plant pathogens which control target weeds. These organisms have been applied to target weeds as sprays either alone or in combination with chemical herbicides. Two mycoherbicides, DEVICE and COLLEGO, have been developed from specific fungal pathogens of weeds and are successful commercial products (Templeton et al., *Reviews of Weed Science* 2:1-14 (1986)). However, bacteria have been commercially developed only in a few cases.

USDA researchers at Washington State University have isolated several bacteria which attack the roots of downybrome (Elliott and Kennedy, U.S. Pat. No. 5,030,562 (1991)). These bacteria are *Pseudomonas spp.* isolated from the rhizosphere/rhizoplane of several crop and weed species. A field study in 1988 indicated that one bacterial isolate (D7) reduced downy brome biomass by more than 50%, thus increasing the competitiveness of the wheat. The enhanced competitiveness resulted in a 35% yield increase compared to untreated wheat (Kennedy et al., *Soil Science of America Journal* 55:722-727 (1991)).

Although the use of plant-suppressive rhizobacteria has been reported for downy brome in the Pacific Northwest, the ability of these microorganisms to consistently control downy brome under the harsher conditions (higher temperatures and lower moisture) which exist in the Central Great Plains was not assessed. The ability of these bacteria to successfully inhibit weed growth depends upon many characteristics, including the cultural and climatic conditions present at the site, and the unique conditions during the inhibitory process. Therefore, the ability of a particular microorganism to reduce the growth of a weed cannot be predicted from the behavior of other microorganisms used for similar purposes.

SUMMARY OF THE INVENTION

The present invention is directed to isolated and preferably purified strains of bacteria having the ability to control the weeds downy brome, Japanese brome, and/or jointed goatgrass while not adversely affecting wheat, especially semidwarf wheat varieties. The bacteria were isolated from soil and plant roots, and have been identified as Pseudomonas putida (FH160), Enterobacter taylorae (FH650), and Xanthomonas maltophilia (FH131). In this connection, the invention embraces the isolation and use of both the pure strains identified above, as well as modified versions thereof. Such modifications are known in the art, and could involve, e.g., mutagenesis or recombinant genetic manipulations such as gene insertion to enhance inhibitory activity. Accordingly, reference in the present specification and claims to the above identified bacteria is intended to cover both the pure strains and all such modifications thereof.

In use, the above bacteria or a mixture thereof may be used for controlling weeds in the area of planted wheat. Such method involves applying to a wheat area an effective weed controlling amount of one of the defined strains or a mixture thereof. Such application can be made by surface spraying a solution of the bacteria having from about $10^7$–$10^{10}$ bacteria per mL at a level of from about 500–1000 mL of solution per acre. In further preferred forms, such a solution may be applied directly to the soil during planting by means of a modified planter. In such cases, the bacterial solution would be applied at a level of from about $10^7$–$10^{10}$ bacteria per meter of planted wheat row.

In addition, the bacteria strains hereof may be mixed with chemical herbicides, and the combination applied for weed control. A wide variety of chemical herbicides can be used in this context, but particularly preferred are the triazine and sulfonylurea herbicides.

DETAILED DESCRIPTION OF THE PREFERRED EMBODIMENTS

Example

The three most preferred strains of soil and rhizoplane bacteria which exhibit effective inhibition of root and shoot growth of downy brome, Japanese brome and/or jointed goatgrass were discovered using the following techniques.

Potential inhibitory bacteria were isolated from the rhizoplane of downy brome and other plants growing in a selected area at the time of sampling, as well as from soil in the same area. The isolation process followed standard procedures. Plant roots were dug from the field sites and roots were gently washed in running water. Either excised roots or soil samples were placed in dilution blanks containing sterile, distilled water and shaken for 20 minutes. After mixing, serial dilutions were prepared and plated on King's B medium supplemented with novobiocin, penicillin, and cycloheximide (Sands and Rovira, *Applied Microbiology* 20:513–514 (1970)) to select for the genus Pseudomonas or closely related bacteria. After incubation at 25° C for 24–48 hours, both fluorescent and nonfluorescent colonies were selected from plates. Isolates were stored frozen until tested for inhibitory activity.

Isolates were initially screened in vitro for inhibitory effects against downy brome, Japanese brome, and jointed goatgrass using the agar plate bioassay method of Kennedy et al. (*Soil Science Society of America Journal* 55:722–727 (1991)), which is incorporated by reference herein.

Individual isolates were inoculated into Pseudomonas minimal salts medium (PMS) (Gasson, *Applied and Environmental Microbiology* 39:25–29 (1980), incorporated by reference herein) and grown at room temperature (about 23° C.) for approximately 24–36 hours (approximately $10^9$ to $10^{10}$ cells per mL of culture medium). The cells were then centrifuged at approximately 6000 rpm for 15 minutes, giving a substantially cell-free culture supernatant.

Inhibition of each weed was then assayed by adding a standard amount of the supernatant (2 ml) to petri plates, then adding a standard amount (20 ml) of 0.9% molten agar (48° C.) to each plate. The contents of the plates were mixed, then allowed to solidify. Control plates were prepared with both PMS medium and distilled water for comparison purposes. After the plates had solidified, the plates were planted with seeds of the weeds of interest. After 5–7 days, both root growth (length) and weed seed germination were determined. The potential inhibitory isolates were also screened against winter wheat in a similar manner to determine that the isolates were not inhibitory to the growth of the crop. Table 1 gives the test results for the three preferred strains.

TABLE 1

Reduction in early root growth of winter wheat, downy brome, Japanese brome, and jointed goatgrass by three inhibitory isolates in agar plate bioassays.[1]

| | % | | | |
|---|---|---|---|---|
| Isolate | Winter Wheat | Downy Brome | Japanese Brome | Jointed Goatgrass |
| FH160 | 16[2] | 67 | 93 | 75 |
| FH131 | 19 | 63 | 11 | 55 |
| FH650 | 10 | 70 | 75 | 60 |

[1] Reduction in root length for each species is expressed as a percent decrease compared to controls.
[2] Numbers are the average of two bioassays.

The three strains found to inhibit at least one of the weeds without inhibiting winter wheat (Table 1) were then screened in growth chamber studies. In this screening, 10-cm-diameter pots were filled with a soil:sand (4:1) mixture, and seeded with either winter wheat (8 seed per pot), jointed goatgrass (8 seed per pot), downy brome (12 seed per pot), or Japanese brome (12 seed per pot). Bacterial isolates were grown in PMS medium, as described previously, and one mL of each culture was added to the seed by dripping the liquid on the soil surface (approximately $10^9$ to $10^{10}$ cells per pot). The seeds were then covered with a layer of the soil:sand mixture and watered as needed throughout the experiment. After approximately 3 weeks, the plants were harvested, roots were washed free of soil, and the roots and shoots of the weeds and wheat were excised and oven-dried at 65° C. for 48 hours to determine dry weights. Dry weights were compared to weights from control pots of the same species treated with either water or the growth medium to determine inhibitory activity. Table 2 sets forth these test results for the preferred bacterial isolates.

TABLE 2

Effects of three inhibitory isolates on shoot and root dry weights of winter wheat, downy brome, and jointed goatgrass in growth chamber experiments.[1]

| | % | | | | | |
|---|---|---|---|---|---|---|
| | Winter Wheat | | Downy Brome | | Jointed Goatgrass | |
| Isolate | Shoot. wt. | Root wt. | Shoot wt. | Root wt. | Shoot wt. | Root wt. |
| FH160 | 22[2] | 20 | 42 | 39 | 0 | 1 |
| FH131 | 6 | +2 | 32 | 30 | — | — |
| FH650 | 9 | 14 | 6 | 5 | 20 | 28 |

[1] Reduction in shoot and root biomass for each species is expressed as a percent decrease or increase (+) compared to controls.
[2] Numbers are the average of two pot experiments with an inoculation rate of $1 \times 10^9$ cells per pot.

Bacterial isolates found to inhibit root and/or shoot growth of downy brome, Japanese brome, or jointed goatgrass in preliminary laboratory and growth chamber studies were next evaluated in the two field studies. In the first field experiment, winter wheat was seeded in four-row plots (1.5 m by 6.0 m). The area had a natural downy brome infestation prior to wheat planting. The isolates were grown in PMS medium as described previously. Prior to wheat emergence, the bacterial isolates were applied to the soil surface at an application rate of approximately $10^9$ bacteria per m² (in water) using a $CO_2$ pressurized backpack sprayer which applied approximately 12.5 gallons of water per acre. Control plots sprayed with water containing only the growth medium with no added bacteria were included for comparison purposes. Table 3 gives the results for isolates FH160 and FH131. Although the wheat yield increases were not statistically different from control treatments, the increases were consistent across all replications.

TABLE 3

Grain yield of winter wheat after field inoculation with two bacterial isoltes inhibitory to downy brome in the 1990-91 growing season.

| Isolate | Yield kg ha$^{-1}$ | Increase % |
|---|---|---|
| Control | 3944 | |
| FH160 | 4455 | +13 |
| FH131 | 4327 | +10 |

In a second study, a unique application method was used to test the inhibitory activity of several bacterial isolates. Downy brome, Japanese brome and jointed goatgrass were planted in 3-row plots of 1.0 m by 4.6 m. Winter wheat was also evaluated in the same manner to insure that the bacterial isolates were not inhibitory to wheat. Bacterial isolates were inoculated onto agar plates of supplemented King's medium as described previously. After growth for approximately 48 hours, sterile 0.1% CaSO$_4$ was added to the plates and the bacterial growth was aseptically scraped from the plates. Bacterial densities were adjusted to approximately 10$^9$ bacteria per mL of medium with additional CaSO$_4$. At planting, the center row of each plot was inoculated with selected isolates by injecting a liquid culture of each isolate into the seed furrow as the seeds were planted. Planting and inoculation was accomplished using a Hege Model 90 6-row plot planter with hoe-type openers modified for liquid inoculation. Each isolate was added to a stainless steel can (2.5 gallon) attached to the planter and fed with compressed air (4 psi). Plastic tubing (0.25 inch I.D.) extended from the can on the back of the planter into the seed zone. A trigger mechanism was used to regulate flow from the can to the seed zone. The application rate was calibrated with application pressure and planter speed so that each bacterial isolate was applied in 0.1% CaSO$_4$ at a rate of approximately 10$^9$ bacteria per meter of row. The seed furrows were closed with a press wheel attached to the planter after inoculation to ensure compaction over the seed zone.

Suppression of each weed species and winter wheat was visually estimated periodically throughout the growing season, and weed and wheat biomass was quantified in the spring and compared to control plots with no added bacteria. The suppressive activity of the three bacterial isolates in April 1992 is shown in Table 4. Significant suppression of downy brome and Japanese brome was observed for all three isolates, but suppression of jointed goatgrass was not observed. No visual differences in weed biomass were observed by June 1992. Harvested weed biomasses also showed no differences due to bacterial inoculation by that time. This was probably due to the fact that wheat was not present to compete with the weeds, and the weeds were able to overcome the inhibitory activity. If wheat had been present in the same plots, the inhibitory activity of the bacteria would probably have been prolonged. The bacterial isolates had no significant effect on wheat grain yields at the end of the growing season (Table 5). However, wheat plots inoculated with isolate FH131 showed an approximate 33% yield increase compared to control plots, but variability between plots resulted in statistical nonsignificance.

TABLE 4

Suppression of downy brome and Japanese brome in field plots with three inhibitory bacterial isolates in the 1991-92 growing seasons.

| | Reduction in Biomass % | |
|---|---|---|
| Isolate | Downy brome | Japanese brome |
| FH160 | 77[1] | 77 |
| FH131 | 73 | 43 |
| FH650 | 73 | 70 |

[1] Reduction in biomass as compared to nontreated paired rows rated in April, 1992. No differences were observed by June, 1992.

TABLE 5

Grain yield of winter wheat after field inoculation with three bacterial isolates inhibitory to downy brome and Japanese brome in the 1991-92 growing season.

| Isolate | Yield kg ha$^{-1}$ | Increase/Decrease % |
|---|---|---|
| Control | 2692 | |
| FH160 | 2564 | −5 |
| FH131 | 3584 | +33 |
| FH650 | 2759 | +2 |

Spontaneous mutants of bacterial isolate FH160 resistant to 100 μg rifampicin L$^{-1}$ (FH160-R) were applied to additional plots to assess bacterial survival in soil and colonization of plant roots. The spontaneous mutants were isolated on a modified King's B medium supplemented with 100 μg rifampicin L$^{-1}$. Only these mutants were able to grow on this particular medium. Plant root samples were taken from plots at the end of the growing season and numbers of antibiotic-resistant bacteria were determined. Isolate FH160-R was found to survive the growing season in inoculated plots in numbers ranging from 10$^3$ to 10$^4$ bacteria per gram of root.

In addition, isolate FH160 was tested in combination with two preemergence herbicides commonly used in winter wheat to determine if the isolate could act synergistically with the herbicides- Two greenhouse experiments were initiated to look at triasulfuron (AMBER) and a herbicide mixture of chlorsulfuron and metsulfuron (FINESSE). Pots were filled with a soil:sand (4:1) mixture, seeded with either downy brome (12 seed per pot) or jointed goatgrass (8 seed per pot), and covered with a layer of the soil:sand mixture. Bacterial isolate FH160 was grown in PMS liquid broth as previously described. The two herbicide treatments were applied at two rates, 3 and 6 g active ingredient per acre. The herbicides were mixed in water, and one mL of bacterial culture (approximately 10$^9$ cells per ml) was added to each treatment. The herbicide/bacteria mixtures were applied using a spray chamber with an application rate of approximately 18 gallons per acre. Pots were watered immediately after treatment to insure movement of the herbicide/bacteria mixtures into the root zone. After approximately 3 weeks, the shoot portion of the plants were excised and oven-dried at 65° C. for 48 hours to determine dry weights. Dry weights were compared to control pots of the same species treated with either no herbicide, no isolate, or no herbicide/no isolate to determine inhibitory and/or synergistic activity. Table 6 shows the results of the first greenhouse experiment. In general, isolate FH160 in combination with FINESSE showed a synergistic reduction of downy brome and jointed goatgrass root growth as compared to either the isolate or the herbicide alone. The second experiment showed similar results.

TABLE 6

Effects of isolate FH160 in combination with two rates of triasulfuron (AMBER) and chlorsulfuron/metsulfuron (FINESSE) herbicides on shoot and root dry weights of downy brome and jointed goatgrass in greenhouse experiments.

| | mg pot$^{-1}$ | | | |
|---|---|---|---|---|
| | Downy Brome | | Jointed Goatgrass | |
| Treatment | Shoot wt. | Root wt. | Shoot wt. | Root wt. |
| H$_2$O—NoH[1] | 64 | 58 | 132 | 147 |
| H$_2$O - A ½ X | 58 | 55 | 119 | 138 |
| H$_2$O - A 1X | 80 | 41 | 101 | 110 |
| H$_2$O - F ½ X | 61 | 52 | 139 | 115 |
| H$_2$O - F 1X | 51 | 43 | 101 | 56 |
| 160 - NoH | 84 | 61 | 73 | 184 |
| 160 - A ½ | 72 | 42 | 116 | 106 |
| 160 - A 1X | 44 | 35 | 124 | 98 |
| 160 - F ½ X | 54 | 29 | 58 | 37 |
| 160 - F 1X | 49 | 24 | 78 | 55 |

[1] H$_2$O = no isolate, NoH = no herbicide, A = AMBER, F = FINESSE, 160 - FH160, ½ X = 3 g active ingredient (ai) per acre, 1X = 6 g ai per acre.

In all experiments, treatments were replicated at least three times in either completely randomized or randomized block designs. All statistical analyses were performed using the Statistical Analysis System (SAS) (Helwig and Council, (eds.), SAS user's guide, SAS Institute, Inc. (1979), incorporated by reference herein). All data were analyzed using analyses of variance. Fisher's (protected) least significant difference test was used for comparison of all treatment means at the 5% level of significance.

The three preferred strains of soil and rhizoplane bacteria have been identified to the level of genus and species by Microbe Inotech Laboratories, Inc. (St. Louis, Mo.) using the Biolog Microplate System ™ for carbon source pattern recognition, Table 7, and gas chromatography of cellular fatty acids. In addition, the strains have been differentiated using genetic fingerprinting as described in Table 8. The bacteria have been identified as *Pseudomonas putida* (FH160), *Enterobacter taylorae* (FH650), and *Xanthomonas maltophilia* (FH131). These strains have been deposited in the American Type Culture Collection, 12301 Parklawn Dr., Rockville, Md., 20852 on Feb. 10, 1993, and have been assigned the following Accession Nos. 55392 (FH160), 55391 (FH650) and 390 (FH131).

TABLE 7

Summary of substrate utilization data.

| Substrate | *P. putida* strain FH160 | *X. maltophilia* strain FH131 | *E. taylorae* strain FH650 |
|---|---|---|---|
| αacyclodextrin | − | − | +/− |
| dextrin | − | + | + |
| glycogen | − | + | + |
| tween40 | + | + | + |
| tween80 | + | − | + |
| N-acetyl-D-galactosamine | − | + | + |
| N-acetyl-D-glucosamine | − | + | + |
| adonitol | − | − | − |
| L-arabinose | + | − | + |
| D-arabitol | +/− | − | − |
| cellobiose | − | − | + |
| i-erythritol | − | − | − |
| D-fructose | + | + | + |
| L-fucose | − | − | + |
| D-galactose | + | − | + |
| gentiobiose | − | +/− | + |
| α-D-glucose | + | − | + |
| m-inositol | + | − | + |
| α-D-lactose | − | − | + |
| lactulose | − | − | +/− |
| maltose | − | + | + |
| D-mannitol | + | − | + |
| D-mannose | + | + | + |
| D-melibiose | − | − | + |
| β-methyl-D-glucoside | − | − | + |
| D-psicose | − | − | + |
| D-raffinose | − | − | − |
| L-rhamnose | − | − | + |
| D-sorbitol | +/− | − | + |
| sucrose | + | − | + |
| trehalose | + | − | + |
| turanose | − | − | + |
| xylitol | − | − | − |
| methyl pyruvate | +/− | − | + |
| mono-methyl-succinate | + | − | + |
| acetic acid | + | + | + |
| cis-aconitic acid | + | + | + |
| citric acid | + | + | + |
| formic acid | − | − | + |
| D-galatonic acid lactone | +, | − | + |
| D-galacturonic acid | + | − | + |
| D-gluconic acid | + | − | + |
| D-glucosaminic acid | +/− | − | +/− |
| D-glucuronic acid | +/− | − | + |
| α-hydroxybutyric acid | − | − | +/− |
| β-hydroxybutyric acid | + | − | + |
| γ-hydroxybutyric acid | − | − | − |
| p-hydroxy phenylacetic acid | − | − | + |
| itaconic acid | − | − | − |
| α-keto butyric acid | − | − | − |
| α-keto glutaric acid | + | − | − |
| α-keto valeric acid | − | − | − |
| D,L-lactic acid | + | + | + |
| malonic acid | +/− | − | + |
| propionic acid | +/− | + | − |
| quinic acid | + | − | − |
| sacchic acid | + | − | + |
| sebacid acid | − | − | − |
| succinic acid | + | + | + |
| bromo succinic acid | + | + | + |
| succinamic acid | + | + | +/− |
| glucuronamide | − | − | + |
| alaninamide | − | − | + |
| D-alanine | + | − | + |
| L-alanine | + | − | + |
| L-alanyl-glycine | + | − | + |
| L-asparagine | + | − | + |
| L-aspartic acid | + | − | + |
| L-glutamic acid | + | − | + |
| glycyl-L-aspartic acid | − | − | + |
| glycyl-L-glutamic acid | − | − | + |
| L-histidine | − | − | + |
| hydroxy-L-proline | − | − | − |
| L-leucine | +/− | − | − |
| L-ornithine | + | − | + |
| L-phenylalanine | − | − | + |
| L-proline | + | − | + |
| L-pyroglutamic acid | + | − | − |
| D-serine | − | − | + |
| L-serine | + | − | + |
| L-thereonine | − | − | + |
| D,L-carnitine | − | − | − |
| γ-amino butyric acid | + | − | − |
| urocanic acid | + | − | + |
| inosine | + | − | + |
| uridine | +/− | − | + |
| thymidine | − | − | + |
| phenyl ethylamine | − | − | +/− |
| putrescine | − | − | − |
| 2-amino ethoanol | +/− | − | − |
| 2,3-butanediol | − | − | − |
| glycerol | + | − | + |
| D,L-α-glycerol phosphate | − | − | + |
| glucose-1-phosphate | − | − | + |

TABLE 7-continued

Summary of substrate utilization data.

| Substrate | P. putida strain FH160 | X. maltophilia strain FH131 | E. taylorae strain FH650 |
|---|---|---|---|
| glucose-6-phosphate | − | − | + |

TABLE 8

Restriction enzyme digestion or genomic DNA from six bacterial isolates.

| Lane 1: | 1 kb ladder marker | |
|---|---|---|
| Lane 2: | DNA was cut with EcoRi | |
| | FH160 | Pseudomonas putida |
| | FH131 | Xanthomonas maltophilia |
| | FH650 | Enterobacter taylorae |
| | D7 | Pseudomonas fluorescens |
| | PF5 | Pseudomonas fluorescens |
| | 2W5 | Pseudomonas aureofaciens |
| Lane 8–13: | DNA was cut with BamHi | |
| | FH160 | Pseudomonas putida |
| | FH131 | Xanthomonas maltophilia |

TABLE 8-continued

Restriction enzyme digestion or genomic DNA from six bacterial isolates.

| FH650 | Enterobacter taylorae |
|---|---|
| D7 | Pseudomonas fluorescens |
| PF5 | Pseudomonas fluorescens |
| 2W5 | Pseudomonas aureofaciens |

We claim:

1. An isolated strain of bacteria having the ability to control the weeds downy brome, Japanese brome and/or jointed goatgrass, said bacteria strain being selected from the group consisting of *Pseudomonas putida* ATCC Accession No. 55392, *Enterobacter taylorae* ATCC Accession No. 55391, *Xanthomonas maltophilia* ATCC Accession No. 55390, mutants thereof having the ability to control said weeds and mixtures thereof.

2. An isolated strain of bacteria identified as *Pseudomonas putida* ATCC Accession No. 55392.

3. An isolated strain of bacteria identified as *Enterobacter taylorae* ATCC Accession No. 55391.

4. An isolated strain of bacteria identified as *Xanthomonas maltophilia* ATCC Accession No. 55390.

* * * * *